(12) United States Patent
Pradhan

(10) Patent No.: US 8,664,417 B2
(45) Date of Patent: Mar. 4, 2014

(54) PROCESS FOR THE SYNTHESIS OF 4-(DIMETHYLSILYL) BUTYLFERROCENE

(75) Inventor: Braja Sundar Pradhan, Andhra Pradesh (IN)

(73) Assignee: CBZ Chemicals Limited, Essex (GB)

( * ) Notice: Subject to any disclaimer, the term of this patent is extended or adjusted under 35 U.S.C. 154(b) by 120 days.

(21) Appl. No.: 13/502,802

(22) PCT Filed: Oct. 18, 2010

(86) PCT No.: PCT/IN2010/000684
§ 371 (c)(1),
(2), (4) Date: Apr. 19, 2012

(87) PCT Pub. No.: WO2011/048615
PCT Pub. Date: Apr. 28, 2011

(65) Prior Publication Data
US 2012/0209019 A1    Aug. 16, 2012

(30) Foreign Application Priority Data

Oct. 19, 2009  (IN) .......................... 2530/CHE/2009
Jun. 10, 2010  (IN) .......................... 2965/CHE/2010

(51) Int. Cl.
C07F 17/02    (2006.01)
(52) U.S. Cl.
USPC ............................................. 556/11; 556/12
(58) Field of Classification Search
USPC .................................................. 556/11, 12
See application file for complete search history.

(56) References Cited

U.S. PATENT DOCUMENTS

| 3,321,501 | A |   | 5/1967 | Wilkus et al. |
| 4,661,608 | A | * | 4/1987 | Gautier et al. ................. 556/11 |
| 5,190,671 | A | * | 3/1993 | Caubere et al. ............... 210/767 |
| 5,214,175 | A | * | 5/1993 | Gautier et al. ................ 556/144 |
| 5,550,267 | A | * | 8/1996 | Graindorge et al. .......... 556/144 |

FOREIGN PATENT DOCUMENTS

| EP | 0171307 | 6/1986 |
| EP | 0478417 | 4/1992 |
| EP | 0479664 | 4/1992 |
| EP | 0687683 | 12/1995 |

OTHER PUBLICATIONS

International Search Report for International Application No. PCT/IN2010/000684 mailed Feb. 28, 2011.

* cited by examiner

*Primary Examiner* — Porfirio Nazario Gonzalez
(74) *Attorney, Agent, or Firm* — Pearl Cohen Zedek Latzer Baratz LLP

(57) ABSTRACT

The invention provides for a process for the preparation of a silylferrocene compound, comprising the steps of treating ferrocene with a 4-chloroalkyryl chloride in the presence of an lewis acid catalyst and an organic solvent to obtain the acylated product, reducing the acylated product to obtain the 4-chloralkylferrocene, treating the 4-chloralkylferroce with a metal under Grignard reaction conditions to form its corresponding Grignard intermediate compound; and reacting with chloroalkylsilane in-situ to give the silylferrocene compound. The silylferrocene compound 4-(dimethylsilyl)butylferrocene can be prepared by the process of the invention.

15 Claims, No Drawings

PROCESS FOR THE SYNTHESIS OF 4-(DIMETHYLSILYL) BUTYLFERROCENE

CROSS-REFERENCE TO RELATED APPLICATIONS

This application is a National Phase Application of PCT International Application No. PCT/IN2010/000684, International Filing Date Oct. 18, 2010, claiming priority of Indian Patent Applications Nos. 2530/CHE/2009, filed Oct. 19, 2009, and 2965/CHE/2010, filed Oct. 6, 2010, both of which are incorporated herein in their entireties.

TECHNICAL FIELD

This invention relates to silylferrocene compounds, more particularly to the 4-(dimethylsilyl)butylferrocene.

BACKGROUND ART

Ferrocenes have been employed for a very long time as combustion catalysts in propellant compositions. It has been found that their properties are improved by the addition of organosilyl radicals bound directly by carbon-silicon bonds to the cyclopentadienyl nucleus of the ferrocene. Such compounds are described, particularly in French Patent. Nos. 1,396,272, 1,396,273 and 2,567,890.

To synthesize these products several processes have already been described, in particular in the above mentioned French patents. The French patent FR 1,398, 235 describes a process for obtaining organosilylmetallocene by employing a reaction of acylation of metallocene using a silyl carboxylic acid halide, the carbonyl group being then reduced to a methylene radical using $LiAlH_4$ as a reducing agent. This process makes it possible to synthesize the silylmetallocene but in low yields, approximately 20% of the acylation reaction.

The French Patent FR 2,567,890 describes a process for the manufacture of silylmetallocene compounds (e.g. dimethylsilyltetramethyleneferrocene) by hydrosilylation of metallocene compounds with $H_2PtCl_6$ catalyst and reduction of the resultant product to obtain silylmetallocene compounds.

The French Patent Nos. 2,667,318, 2,667,600 and 2,721, 028 discloses the process for the synthesis of monohaloalkylferrocenes, an intermediate used in the synthesis of silylferrocene compounds. The French Patent FR 2,667,318 describes a process for the synthesis of monohaloalkylferrocenes by catalytic hydrogenation over $PtO_2$ in acetic acid of monohaloalkanoylferrocenes. The crude synthetic product thus obtained, with purity generally in the region of 95%, requires subsequent purification in order to be used as an intermediate in the synthesis of ferrocene combustion catalysts for propellants. However, for this to be the case, it is necessary, as is shown in the Examples, to use a recrystallized, and thus very pure, starting haloalkanoylferrocene. Moreover, it turns out in practice that a purity of 95% is limiting for the above mentioned use and that it is preferable to use a haloalkylferrocene with a purity of 98%. Further, the platinum-based catalyst is fairly expensive and hydrogenation under pressure requires relatively expensive specific equipment.

The French Patent FR 2,667,600 describes the production, according to the abovementioned "Friedel-Crafts" method, of a crude synthetic haloalkanoylferrocene derivative, having purity generally in the region of 95%, by a combination of very precise operating conditions, in particular as regards the temperature, the concentration and the amount of the reactants. The crude product thus obtained is, however, insufficiently pure to be used directly, without purification, in the above mentioned process as described in French Patent FR 2,667,318. Such an use would lead, in fact, to a crude haloalkylferrocene derivative with a purity markedly less than 95% which cannot be used as is without prior purification in carrying out the subsequent stages.

The French Patent FR 2,667,600 certainly mentions that the addition of a cerous salt makes it possible to obtain a crude product with a purity greater than 95%, but this addition has virtually no influence on the content of 1,1'-di(haloalkanoyl) ferrocene, derivative, which remains excessively high.

The French Patent FR 2,721,028 describes a process for the synthesis of haloalkylferrocenes, comprising a first stage of reaction, in the presence of aluminum chloride as catalyst and inorganic solvent medium, of a haloalkyl carboxylic acid halide or haloalkylcarboxylic acid anhydride with a ferrocene derivative to produce an intermediate compound which is thereafter reduced with metal hydride to provide the haloalkylferrocene.

Thus, there exists a need for an improved process for preparation silylmetallocene compounds, such as for example 4-(dimethylsilyl)butylferrocene.

SUMMARY OF THE INVENTION

Accordingly the present invention provides an improved process for the preparation of a silylferrocene compound, comprising the steps of treating ferrocene with a 4-chloroalkyryl chloride in the presence of an lewis acid catalyst and an organic solvent to obtain the acylated product; reducing the acylated product to obtain the 4-chloralkylferrocene; treating the 4-chloroalkylferroce with a metal under Grignard reaction conditions to form the corresponding Grignard intermediate compound; and reacting with chloroalkylsilane in-situ to give the silylferrocene compound.

Further, the invention provides an improved process for the preparation of 4-(dimethylsilyl)butylferrocene, which comprises the steps of:

treating ferrocene with 4-chlorobutyryl chloride in an organic solvent medium in the presence of aluminum chloride catalyst to produce 1-oxo-4-chlorobutylferrocene formula I;

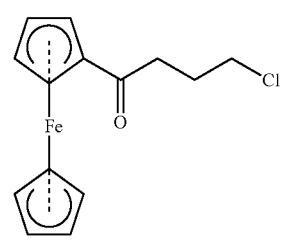

subjecting an alcoholic solution of 1-oxo-4-chlorobutylferrocene I to a step of treatment with zinc mercuric chloride amalgam to produce an intermediate, 4-chlorobuytylferrocene II;

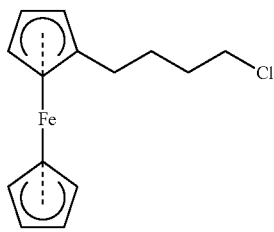
II adding the 4-chlorobuytylferrocene II to a Grignard reaction mixture to form its corresponding Grignard intermediate compound which reacts with chlorodimethylsilane in situ to give 4-(dimethylsilyl)butylferrocene.

Furthermore, the present invention provides a process for the preparation of 4-(dimethylsilyl)butylferrocene, which comprises the steps of:

treating ferrocene with 4-chlorobutyryl chloride in an organic solvent medium in the presence of aluminum chloride catalyst to produce 1-oxo-4-chlorobutylferrocene formula I;

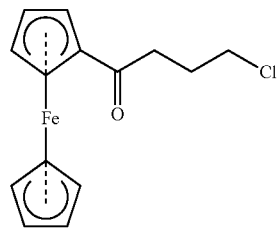
I reductive decarbonylation of 1-oxo-4-chlorobutylferrocene in the presence of sodium trifluoroacetoxyborohydride to produce an intermediate, 4-chlorobutylferrocene II;

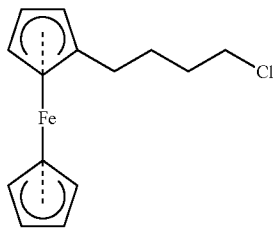
II adding the 4-chlorobutylferrocene II to a Grignard reaction mixture to form its corresponding Grignard intermediate compound which reacts with chlorodimethylsilane in situ to give 4-(dimethylsilyl)butylferrocene.

DETAILED DESCRIPTION

The invention provides for a process for the preparation of a silylferrocene compound. The process comprises treating ferrocene with a 4-chloroalkyryl chloride in the presence of an acid catalyst and an organic solvent to obtain the acylated product, reduction of the acylated product to obtain the 4-chloralkylferrocene, which on treatment with a metal under Grignard type reaction conditions forms the corresponding Grignard intermediate compound which can be reacted with chloroalkylsilane in-situ to furnish the silylferrocene compound.

The process further comprises treating ferrocene with a 4-chloroalkyryl chloride in the presence of an acid catalyst and an organic solvent to obtain the acylated product, reduction of the acylated product to obtain the 4-chloralkylferrocene, which on treatment with a metal under Grignard type reaction conditions forms the corresponding Grignard intermediate compound which can be reacted with chloroalkylsilane in-situ to give the silylferrocene compound.

Examples of silylferrocene compounds prepared by the process of the invention include ferrocene compounds wherein the alkyryl group can be selected from the group consisting of alkyryl halides. Catalyst includes lewis acid type and organic solvents include aliphatic.halides. Metal for Grignard reaction are those known in the art and include without limitation Mg, Li, more particularly, Mg. Examples of silylferrocene compounds prepared by the process of the invention include 4(dimethylsilyl)butylferrocene.

In a specific embodiment, a silylferrocene compound such as 4-(dimethylsilyl)butylferrocene can be prepared. The process for the preparation of 4-(dimethylsilyl)butylferrocene comprises (a) treating ferrocene with 4-chlorobutyryl chloride, in the presence of aluminum chloride catalyst and an organic solvent to obtain the acylated product, 4-chlorobutyroylferrocene; (b) reduction of 4-chlorobutyroylferrocene to yield 4-chlorobutylferrocene, using without limitation a Clemmensen type reduction; (c) treating 4-chlorobutylferrocene with a metal such as a magnesium under Grignard reaction conditions to form the corresponding Grignard intermediate compound which when reacted with chlorodimethylsilane in-situ yields 4-(dimethylsilyl)butylferrocene.

In another embodiment, the preparation of 4-Dimethylsilyl)butylferrocene comprises of three reaction stages. The first reaction stage consists of a reaction of Friedel-Crafts reaction in, which ferrocene was treated with 4-chlorobutyryl chloride in the presence of aluminum chloride catalyst and an organic solvent to obtain the acylated product, 1-oxo-4-chlorobutylferrocene. Dichloromethane is the organic solvent which is commonly used in the Friedel-Crafts acylation reaction. The other solvents commonly used for this type of reaction are also suitable. Mention may be made, for example of chlorinated solvents such as dichloroethane or chloroform or a combination thereof.

In another embodiment the invention provides for a process for preparing 1-oxo-4-chlorobutylferrocene. The process comprises adding chlobutyryl chloride in anhydrous dichloromethane to a solution of ferrocene in anhydrous dichloromethane over a period of 1-2 hr to form a mixture; adding aluminum chloride to the mixture, at −20° C. to −5° C. over a period of 2-5 h under stirring; pouring the reaction mixture on ice; washing the organic layer and then drying the same; and subjecting the dried residue to the step of solidification under vacuum to produce the final product, 1-oxo-4-chlorobutylferrocene. The step of washing is performed using water, 10% aqueous sodium hydroxide solution, water, 10% aqueous sodium hydroxide solution, water, dilute hydrochloric acid, water and finally with brine.

In the second reaction stage 1-oxo-4-chlorobutylferrocene was reduced in the presence of zinc amalgam and an alcoholic solvent to obtain 4-chlorobutylferrocene (Clemmensen's reduction). The alcoholic solvent used in the preparation of the 4-chlorobutylferrocene can be selected from the group comprising n-butanol, isopropyl alcohol, n-propanol, tert-butanol, methanol, or ethanol or a combination thereof.

In another embodiment the invention provides a process for preparing 4-chlorobutylferrocene, the process comprises adding freshly prepared zinc mercuric chloride amalgam to an alcoholic solution of the said 1-oxo-4-chlorobutylferrocene at room temperature to form a mixture, adding concentrated hydrochloric acid to the mixture; heating the mixture at a temperature range of 25-70° C.; filtering the reaction mixture to remove deactivated zinc-amalgam and washing the same with isopropyl alcohol; concentrating the filtrate and the washings to obtain a residue; diluting the residue to the step of dilution with water and extracting with a solvent; washing the extract and drying it over sodium sulfate to produce the desired product 4-chlorobutylferrocene In another embodiment the invention provides for a process for preparing zinc mercuric chloride amalgam, the process comprises the steps: adding zinc dust to an aqueous solution of sodium hydroxide in water to form a slurry under stirring at room temperature, to form a residue; washing the residue with water till the washings were neutral; adding mercuric chloride to the zinc residue under stirring; subjecting the residue to the step of washing with water to form the product.

In another embodiment, the reaction was also carried out under milder reaction conditions using, as reactant, sodium trifluoroacetoxyborohydride in place of zinc amalgam which, as mentioned in the preceding paragraph is, usually used in achieving the Clemmensen's reduction. The modified process is advantageous as it is easier to scale-up, environmental-friendly and high-yielding. Since the preparation of zinc-amalgam itself constitutes a step in the synthesis, the new method of synthesis also reduces the number of chemical operations in the process.

In the third reaction stage 4-chlorobutylferrocene was reacted with magnesium metal under Grignard type reaction conditions to form the corresponding Grignard intermediate compound which reacted with chlorodimethylsilane in-situ to give 4-(dimethylsilyl)butylferrocene In another embodiment the invention provides a process for preparing 4-(dimethylsilyl)butylferrocene the process comprises the steps of: adding diethylether to a mixture of magnesium turnings and iodine to form a mixture, adding 1,2-dibromoethane to the mixture at room temperature; treating the ferrocene derivative II with the reaction mixture; subjecting the reaction mixture to the step of heating at 40-45° C.; cooling the reaction mixture to −10° C. to −15° C., adding chlorodimethylsilane to the reaction mixture; subjecting the mixture to the step of stirring and pouring the same on ice containing ammonium chloride; extracting the aqueous layer with ethyl acetate; mixing both the extracts and washing them; subjecting the washed mixture to the step of drying over sodium sulfate to produce the final product in liquid form. The step of washing is carried out by using water, saturated sodium bicarbonate solution, and brine In another embodiment the invention provides a process for preparing 4-(dimethylsilyl)butylferrocene the process comprises the steps of: adding tetrahydrofuran to a mixture of magnesium turnings and iodine to form a mixture, adding 1,2-dibromoethane to the mixture at room temperature; treating the ferrocene derivative II with the reaction mixture; subjecting the reaction mixture to the step of heating at 40-45° C.; cooling the reaction mixture to −10° C. to −15° C., adding chlorodimethylsilane to the reaction mixture; subjecting the mixture to the step of stirring and pouring the same on ice containing ammonium chloride; extracting the aqueous layer with ethyl acetate; mixing both the extracts and washing them; subjecting the washed mixture to the step of drying over sodium sulfate to produce the final product in liquid form. The step of washing is carried out by using water, saturated sodium bicarbonate solution, and brine.

This process is simpler in term of industrial operation and the can be easily scaled up at industrial level.

Hereinafter the invention is explained more specifically referring to the working examples, but is not restricted to the same.

Example 1

Preparation of 1-oxo-4-chlorobutylferrocene I 4-chlobutyryl chloride (100 g, 709.2 mmole) in anhydrous dichloromethane (200 ml) was added to a solution of ferrocene (100 g, 537.5 mmole) in anhydrous dichloromethane (6200 ml) over a period of 1.5 h at −20° C. Aluminum chloride (85.92 g, 596.83 mmole) was then added batchwise to the reaction mixture at −20° C. over a period of 2 h and the mixture stirred for another 2 h at this, temperature by which time the reaction was almost complete as indicated by TLC.

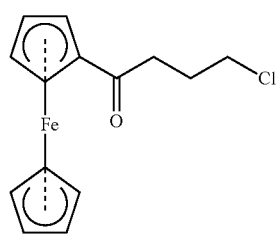

I

The reaction mixture was then poured onto crushed ice to quench the reaction. The organic layer was washed successively with water (10×100 ml), 10% aqueous sodium hydroxide solution (2×100 ml), water (2×100 ml), dilute hydrochloric acid (2×100 ml), water (2×100 ml), saturated sodium bicarbonate solution (1×100 ml), water (2×100 ml) and finally with brine (1×100 ml). The organic layer was then dried over sodium sulfate and concentrated to recover dichloromethane. The residue was allowed to solidify under vacuum to give the desired compound I as a red coloured solid; yield: 140 g, 89%.

It is to be noted that either of the experiments set forth in Examples 2, 3 or 3A may be followed. However, the experiments set forth in Example 3A are preferred since the reaction was carried out under milder reaction conditions using, as reactant, sodium trifluoroacetoxyborohydride in place of zinc amalgam which is a modified process as being advantageous as it is easier to scale-up, environmental friendly and high yielding. Since the preparation of zinc-amalgam itself constitutes a step in the synthesis, it also reduces the number of chemical operations in the process.

Either of the experiments in Examples 2(a) or 2(b), may be followed for conducting the Clemmensen's reduction, the experiment in Example 2(a) may be preferred because it uses a catalytic amount of mercuric chloride.

Example 2a

Preparation of 4-Chlorobutylferrocene II

A slurry of freshly prepared zinc-mercuric chloride amalgam, which was prepared from zinc dust (250 g, 3.83 mole) and mercuric chloride (4.67 g, 17.2 mmole) following the procedure detailed at the end of this experiment, in concentrated hydrochloric acid (150 ml) was added to a solution of the ferrocene derivative I (250 g, 858.22 mmole) in isopropyl alcohol (1.5 lt) at room temperature. Another batch of concentrated hydrochloric acid (350 ml) was added to the reaction mixture over a period of 30 minutes. The reaction mixture was then heated to 60-65° C. and maintained at this temperature for 4 h by which time the reaction was complete as indicated from TLC.

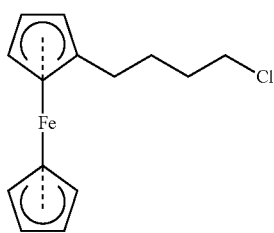

II

The reaction mixture was filtered to remove deactivated zinc-amalgam which was washed with isopropyl alcohol (300 ml). The filtrate and the washings were combined and concentrated under reduced pressure recovering isopropyl alcohol. The residue was diluted with water (700 ml) and extracted with n-hexane (5×300 ml). The combined extract was washed successively with water (2×500 ml), 10% aqueous sodium hydroxide solution (2×200 ml), water (2×300 ml), 5% aqueous hydrochloric acid (2×300 ml), water (2×300 ml) and brine (2×200 ml). The organic layer was then dried over sodium sulfate and concentrated to give the desired reduced product II as an oil yield 169 g (71%). The material was carried over to the following step without further purification.

Example 2b

Preparation of 4-Chlorobutylferrocene II

A slurry of freshly prepared zinc-mercuric chloride amalgam, which was prepared from zinc dust (200 g, 3.06 mole) and mercuric chloride (20 g, 73.66 mmole) following the procedure detailed at the end of this experiment, in concentrated hydrochloric acid (200 ml) was added to a solution of the ferrocene derivative I (100 g, 343.29 mmole) in n-butyl alcohol (1.0 lt) at room temperature. The reaction mixture was then heated to 60-70° C. and maintained at this temperature for 2 h by which time the reaction was complete as indicated from TLC.

The reaction mixture was filtered to remove deactivated zinc-amalgam which was washed with n-butyl alcohol. The filtrate and the washings were combined and concentrated under reduced pressure recovering n-butyl alcohol. The residue was diluted with water (700 ml) and extracted with n-hexane (5×300 ml). The combined extract was washed successively with water (2×500 ml), 10% aqueous sodium hydroxide solution (2×1.5 lt), water (3×1.5 lt), 5% aqueous hydrochloric acid (2×1.5 lt), water (2×1.5 lt), saturated sodium bicarbonate solution (1×1.5 lt), water (2×1.5 lt) and brine (1×1.5 lt). The organic layer was then dried over sodium sulfate and concentrated to give the desired reduced product II as an oil; yield 90 g, 90%.

The material was pure enough to be carried over to the following step without any further purification.

Example 3

Preparation of Zinc-Mercuric Chloride Amalgam

Zinc dust (250 g, 3.83 mole) was added to an aqueous solution of sodium hydroxide (125 g, 3 mole) in water (1.25 lt) and the slurry was stirred at room temperature for 1 h. The aqueous sodium hydroxide solution was decanted off and the residue was washed repeatedly with water (5×1.2 lt) when the pH of the washings became neutral to litmus paper. A solution of mercuric chloride (4.67 g, 17.2 mmole) in water (450 ml) was then added to the zinc residue and the reaction mixture stirred for 1 h at room temperature. Water was decanted off from the reaction mixture and the residue was washed with water (1×1 lt) to give activated zinc-amalgam.

Example 3A

Preparation of 4-Chlorobutylferrocene II

Sodium trifluoroacetoxyborohydride was prepared in situ from trifluroacetic acid and sodium borohydride, which means the operation was carried out in a single pot.

A cold solution of freshly distilled trifluoroacetic acid (5 ml) was added to a solution of the ferrocene derivative, 1-Oxo-4-chlorobutylferrocene I, (5 g, 17.2 mmole) in dry dichloromethane (15 ml) at 0° C. Sodium borohydride (0.78 g) was added to the reaction mixture at 0° C. and the reaction mixture was stirred overnight at this temperature. After completion of the reaction as indicated from TLC, the reaction was quenched by adding water (50 ml) and the mixture was extracted with dichloromethane (2×25 ml).

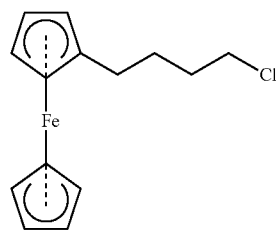

II

The organic layer was washed with a saturated solution of sodium bicarbonate, brine, dried over sodium sulfate and concentrated to give the product II as viscous oil; yield: 3.3 g, 70%.

Example 4

Preparation of 4-(Dimethylsilyl)butylferrocene III

Diethylether or tetrahydrofuran (250 ml) was added to a mixture of magnesium turnings (40 g, 1.64 mole) and a catalytic amount of iodine (0.1 g, 0.39 mmole). 1,2-Dibromoethane (34 ml, 394 mole) was then added to the reaction mixture over a period of 30+ minutes at room temperature. The ferrocene derivative II (115 g, 415 mmole) in diethylether or tetrahydrofuran (250 ml) was added to the reaction mixture at room temperature in such a manner that the reaction mixture refluxed gently. After the completion of the addition, the reaction mixture was heated to 40-45° C. After 5 h at reflux, the heating bath was removed and the reaction mixture was cooled to −10 to −15° C. Chlorodimethylsilane (59.06 g, 624 mole) was then added to the reaction mixture at this temperature over a period of 35 minutes. After completion of addition, the mixture was allowed to warm up to the room temperature and stirred overnight at this temperature when reaction completed as indicated from TLC.

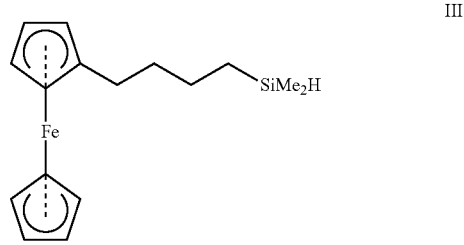

The reaction mixture was then poured onto crushed ice (500 g) containing ammonium chloride (25 g) and the mixture stirred vigourously to facilitate separation of layers. The organic layer was concentrated to a thick liquid. The aqueous layer was extracted with ethyl acetate (3×90 ml) and the extract was combined with the thick liquid. The combined extract was washed successively with water (1×200 ml), saturated sodium bicarbonate solution (1×200 ml), water (1×200 ml) and brine (1×200 ml), dried over sodium (1×200 ml) and concentrated under reduced pressure to give the silane III as a thick liquid; yield: (119 g, 95%).

I claim:

1. A process for the preparation of a silylferrocene compound, comprising the steps of treating ferrocene with a 4-chloroalkyryl chloride in the presence of an acid catalyst and an organic solvent to obtain the acylated product,
reducing the acylated product to obtain the 4-chloralkylferrocene,
treating the 4-chloroalkylferrocene with a metal under Grignard type reaction conditions to form the corresponding Grignard intermediate compound; and
reacting with chloroalkylsilane in-situ to give the silylferrocene compound.

2. The process of claim 1, wherein the silylferrocene compound is 4-(dimethylsilyl)butylferrocene.

3. The process of claim 1, wherein the 4-chloroalkyryl chloride is 4-chlorobutyryl chloride.

4. The process of claim 1, wherein the organic solvent is selected from the group consisting of dichloromethane, dichloroethane, chloroform or a combination thereof.

5. A process for the preparation of 4-(dimethylsilyl)butylferrocene, which comprises the steps of:
treating ferrocene with 4-chlorobutyryl chloride in an organic solvent medium in the presence of aluminum chloride catalyst to produce 1-oxo-4-chlorobutylferrocene formula I;

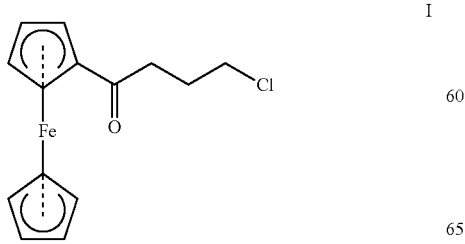

subjecting an alcoholic solution of 1-oxo-4-chlorobutylferrocene I to a step of treatment with zinc mercuric chloride amalgam to produce an intermediate, 4-chlorobuytylferrocene II;

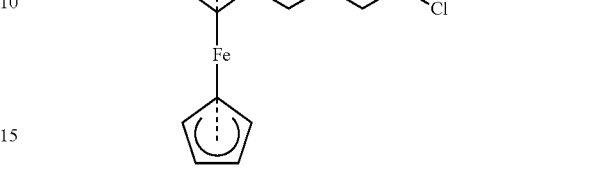

adding the 4-chlorobuytylferrocene II to a Grignard type reaction mixture to form the corresponding Grignard intermediate compound which reacts with chlorodimethylsilane in situ to give 4-(dimethylsilyl)butylferrocene.

6. The process of claim 5, wherein the organic solvent is selected from the group consisting of dichloromethane, dichloroethane, chloroform or a combination thereof.

7. The process of claim 5, wherein the preparation of said 1-Oxo-4-chlorobutyl-ferrocene is carried out at a temperature in the range from about −20° C. to about −5° C.

8. The process of claim 5, wherein the alcoholic solvent used in the preparation of said 4-chlorobutylferrocene comprises of n-butanol, isopropyl alcohol, n-propanol, tert-butanol, methanol, ethanol or a combination thereof.

9. The process of claim 5, wherein the preparation of 4-chlorobutylferrocene is carried out at a temperature in the range from about 25° C. to about 70° C.

10. The process of claim 5, wherein the Grignard type reaction mixture comprises diethylether or tetrahydrofuran, magnesium turnings, iodine, and 1,2-dibromoethane.

11. A process for the preparation of 4-(dimethylsilyl)butylferrocene, which comprises the steps of:
treating ferrocene with 4-chlorobutyryl chloride in an organic solvent medium in the presence of aluminum chloride catalyst to produce 1-oxo-4-chlorobutylferrocene formula I;

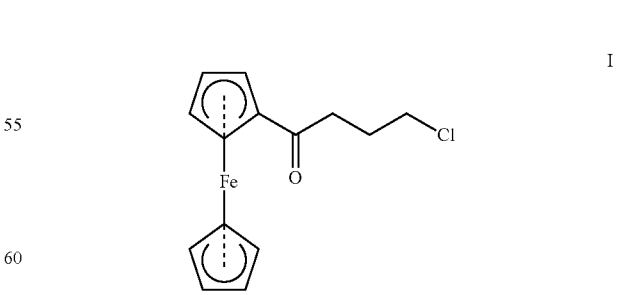

reductive decarbonylation of 1-oxo-4-chlorobutylferrocene in the presence of sodium trifluoroacetoxyborohydride to produce an intermediate, 4-chlorobuytylferrocene II;

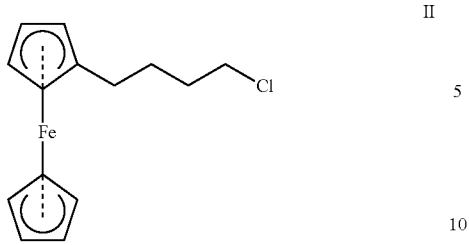

II adding the 4-chlorobuytylferrocene II to a Grignard reaction mixture to form the corresponding Grignard type intermediate compound which reacts with chlorodimethylsilane in situ to give 4-(dimethylsilyl)butylferrocene.

12. The process of claim 11, wherein the organic solvent used in the preparation of 1-oxo-4-chlorobutylferrocene comprises dichloromethane, dichloroethane or chloroform or a combination thereof.

13. The process of claim 11 wherein the preparation of said 1-oxo-4-chlorobutyl-ferrocene is carried out at a temperature in the range from about −20° C. to about −5° C.

14. The process of claim 11, wherein sodium trifluoroacetoxyborohydride is prepared in situ from trifluroacetic acid and sodium borohydride.

15. The process of claim 11, wherein the Grignard type reaction mixture comprises diethylether or tetrahydrofuran, magnesium turnings, iodine, and 1,2-dibromoethane.

* * * * *